United States Patent [19]

Tomita et al.

[11] Patent Number: 5,322,836

[45] Date of Patent: Jun. 21, 1994

[54] BIOACTIVE AGENTS, COMPOSITIONS AND MATERIALS COMPRISING SAID BIOACTIVE AGENTS

[75] Inventors: Mamoru Tomita; Seiichi Shimamura, both of Yokohama; Yasuo Fukuwatari, Kawasaki; Hiroshi Miyakawa, Kamakura; Hitoshi Saito, Warabi, all of Japan

[73] Assignee: Morinaga Milk Industry Co., Ltd., Tokyo, Japan

[21] Appl. No.: 917,693

[22] Filed: Mar. 6, 1991

Related U.S. Application Data

[62] Division of Ser. No. 484,240, Feb. 26, 1990, abandoned.

[30] Foreign Application Priority Data

Feb. 27, 1989 [JP] Japan .................... 1-48297

[51] Int. Cl.$^5$ .................... A61K 37/14; A23C 17/00; A23C 9/12
[52] U.S. Cl. .................... 514/6; 426/34; 426/43; 426/61; 426/583; 426/657; 435/253.6; 530/365; 530/366; 530/832
[58] Field of Search .................... 435/253.6; 514/6; 530/365, 366, 832; 426/34, 43, 657, 583, 61

[56] References Cited

U.S. PATENT DOCUMENTS

4,668,771 5/1987 Kawakami et al. .................... 530/395
4,791,193 12/1988 Okonogi et al. .................... 530/365

OTHER PUBLICATIONS

APS Abstract Japanese Patent 01-221319 (1989) Okonogi et al. Pub. Date Abs. Nov. 29, 1989 Patent Sep. 4, 1989.

*Primary Examiner*—Herbert J. Lilling
*Attorney, Agent, or Firm*—Oblon, Spivak, McClelland, Maier & Neustadt

[57] ABSTRACT

Bioactive agents, having growth-promoting activity upon Bifidobacteria, consisting of one or more lactoferrin-compounds selected from the group consisting of bovine lactoferrin, bovine apolactoferrin and bovine Fe-lactoferrin, which can be used as it is as agents to promote proliferation of Bifidobacteria both in vivo and in vitro, and as additives to prepare compositions, materials and products to afford growth-promoting activity thereto, and to improve survivability of Bifidobacteria, if contained therein.

12 Claims, No Drawings

5,322,836

BIOACTIVE AGENTS, COMPOSITIONS AND MATERIALS COMPRISING SAID BIOACTIVE AGENTS

This application is a division of application Ser. No. 07/484,240, filed on Feb. 26, 1990, now abandoned.

FIELD OF THE INVENTION

The present invention relates to bioactive agents having growth-promoting activity to Bifidobacteria and utilization thereof. More particularly, the present invention relates to bioactive agents having growth-promoting activity to Bifidobacteria consisting of one or more lactoferrin-compounds selected from the group consisting of bovine lactoferrin, bovine apolactoferrin and bovine Fe-lactoferrin, as well as compositions and materials comprising said bioactive agent as an effective component.

BACKGROUND OF THE INVENTION

Bifidobacteria are known as useful microorganisms in the intestine of animals inclusive of human beings, and their usefulness has been clinically proved, for example, for therapy or prevention of various symptoms or diseases such as diarrhea, constipation and infectious diseases, and for growth-inhibition against harmful intestinal microorganisms.

Various substances having growth-promoting activity to Bifidobacteria have been reported, for example, N-acetylglucosamine, pantethinic substances, various peptides and nucleic-acid-related substances as well as various saccharides (such as lactulose) which are not digested by gastric acid and which are utilized by Bifidobacteria.

The present invention provides new bioactive agents having growth-promoting activity to Bifidobacteria, which are completely different from those substances which had been known to have growth-promoting activity, and which consist of one or more lactoferrin-compounds selected from the group consisting of bovine lactoferrin, bovine apolactoferrin and bovine Fe-lactoferrin.

Meanwhile, lactoferrin is known as an iron-binding protein occurring, in vivo, in lacrima, saliva, peripheral blood and milk and the like. Lactoferrin content in cow's milk is 1/10 of that in human milk, and it has been known that bovine lactoferrin has antibacterial activity to harmful microorganism belonging to the genuses of Escherichia, Candida and Clostridium and the like [cf: Welsh, J. K. and J. T. May; Journal of Pediatrics; Vol. 94; Page 1; 1979].

It has been reported that bovine apolactoferrin, which is obtainable by unbinding iron from lactoferrin originating from cow's milk, may inhibit proliferation of harmful microorganisms belonging to the genuses of Escherichia, Staphylococcus and Enterococcus and the like in synthetic medium with a concentration of 0.5–30 mg of the apolactoferrin per ml medium [Nonnecke, B. J. and K. L. Smith; Journal of Dairy Science; Vol. 67; Page 606; 1984].

It has been considered in general that apolactoferrin may act to inhibit proliferation of microorganisms, which require iron strongly, due to chelation of iron with apolactoferrin.

On the other hand, it has been known that human Fe-lactoferrin, which is obtainable by saturating human lactoferrin with Fe, may enhance or promote proliferation of Bifidobacteria which are typical and useful microorganisms found in the human intestine [Kodama; Nihon Shohnika Gakukaizasshi (The Journal of Japanese Pediatrics Society); Vol. 87; Page 1000; 1983].

PROBLEMS IN THE PRIOR ART

In the belief of the inventors of the present application, there has been no report referring to growth-promoting activity of bovine lactoferrin to Bifidobacteria.

As will be readily understood, it has been difficult to supply large quantity of human Fe-lactoferrin.

SOLUTION OF THE PROBLEMS

The inventors of the present application have thoroughly studied on lactoferrin, and found that growth-promoting activity of bovine lactoferrin, bovine apolactoferrin and bovine Fe-lactoferrin is stronger than that of human Fe-lactoferrin. The present invention is based on this discovery.

OBJECTS OF THE INVENTION

It is an object of the present invention to provide new and useful bioactive agents, consisting of one or more lactoferrin-compounds selected from the group consisting of bovine lactoferrin, bovine apolactoferrin and bovine Fe-lactoferrin, which are found to have strong growth-promoting activity to Bifidobacteria.

It is another object of the present invention to provide compositions and those materials which comprise the bioactive agent as the effective component and viable Bifidobacteria.

It is a further object of the present invention to provide those materials which comprises the bioactive agents but which do not include viable Bifidobacteria.

SUMMARY OF THE INVENTION

In accordance with the present invention, the bioactive agents consist of one or more lactoferrin-compounds selected from the group consisting of bovine lactoferrin, bovine apolactoferrin and bovine Fe-lactoferrin, and can be prepared in the form of liquid and solid. The bioactive agents in accordance with the present invention may remarkably promote proliferation of Bifidobacteria both in vivo and in vitro.

Thus the bioactive agents of the present invention can be used as drugs to be orally dosed to animals inclusive of humanbeings for prevention and/or therapy against certain infections diseases, as it is or in the form of preparations by adding carriers, vehicles or excipients thereto.

The bioactive agents of the present invention can be also used as additives to compositions and materials to afford growth-promoting activity thereto. The compositions and materials to which the bioactive agents are added can be certainly used not only as drugs, healthy foods, functional foods, healthy feeds to improve their intestinal conditions, but also as those materials in which Bifidobacteria are to be proliferated, for example, culture media for massproduction of viable Bifidobacteria, culture media for determination of viable count of Bifidobacteria, and materials for preparing yogurt or pickles and the like.

The bioactive agents of the present invention can be added to those material in which viable Bifidobacteria are included, for example, yogurt or feeds containing Bifidobacteria. In such cases, the bioactive agents included in the material are effective not only to promote proliferation of Bifidobacteria therein, but also to improve survivability of Bifidobacteria included therein. In other words, coexistence of the bioactive agents and viable Bifidobacteria in the materials may prolong their preservabilities.

DETAILED DESCRIPTION OF THE INVENTION

Bovine apolactoferrin can be prepared from bovine lactoferrin by removing Fe therefrom. Bovine Fe-lactoferrin can be prepared from saturation of bovine apolactoferrin with iron.

Any materials which include bovine lactoferrin can be used as the source of bovine lactoferrin, for example, cow's milk such as colostrum, transitional milk, matured milk and milk in later lactation, as well as processed products thereof (such as skim milk), or by-products obtainable by processing the materials (such as cheese whey) and the like. Bovine lactoferrin can be isolated and purified from these materials, for example, by ion-exchange chromatography. The resultant bovine lactoferrin can be dissolved into citric acid solution to remove iron thereby iron-free lactoferrin (apolactoferrin) can be prepared. The resultant apolactoferrin is dissolved into and reacted with aqueous solution of iron sulfate, then resultant reaction mixture is subjected to ultrafiltration thereby Fe-lactoferrin can be obtained. The resultant Fe-lactoferrin in liquid or solid form can be used as it is as growth-promoting agents for Bifidobacteria. Alternatively, the resultant Fe-lactoferrin can be mixed with inert carriers or fillers in the form of liquid, powder or solid as well as other drugs, foods and feeds or materials therefor and the like to prepare compositions having growth-promoting activity.

Now some exemplifying tests will be described hereunder for better understanding of the present invention.

Test 1

Growth-promoting activity of bovine lactoferrin, bovine apolactoferrin and bovine Fe-lactoferrin to Bifidobacteria was evaluated.

(1) PREPARATION OF SAMPLES (1-1) Preparation of Bovine Lactoferrin

Bovine lactoferrin was prepared in accordance with the conventional method described in Example 2 in Japanese Unexamined Patent Application Gazette No. 63(1988)-152400 which is hereby incorporated into the description of the present invention.

(1-2) Preparation of Apolactoferrin

Into 2100 ml of purified water, 90 g of bovine lactoferrin obtained in the previous step (1-1) was dissolved, and 10% aqueous solution of citric acid was further added thereto to adjust its pH to 2.5, then the resultant liquid was kept for 1 hour at room temperature to remove or unbind iron from lactoferrin. The resultant liquid was subjected to ultrafiltration and the retentate was freeze-dried thereby 87 g of apolactoferrin was obtained.

(1-3) Preparation of Bovine Fe-lactoferrin

Into 700 ml of purified water, 30 g of the bovine lactoferrin obtained in the previous step (1-1) was dissolved, and the resultant solution was reacted with aqueous solution of 2.6 mM iron sulfate for 24 hours at room temperature. The resultant reaction mixture was subjected to ultrafiltration and thus obtained retentate was freeze-dried thereby 26 g of Fe-lactoferrin was harvested.

(1-4) Preparation of Human Fe-lactoferrin

Human Fe-lactoferrin was prepared in accordance with the conventional method by Kodama (cf. The Journal of Japanese Pediatrics Association; Vol. 87; page 1000; 1983)

(2) TESTED STRAINS

Following strains were used for tests.
① Bifidobacterium bifidum: ATCC 15696
② Bifidobacterium infantis: ATCC 15697
③ Bifidobacterium breve: ATCC 15700
④ Bifidobacterium longum: ATCC 15707
⑤ Bifidobacterium pseudolongum: ATCC 25526
⑥ Bifidobacterium animalis: ATCC 25527

It should be noted that specific microbial strains deposited to the competent depository were used in the test for eliminating troublesome jobs, for example collection of microorganisms from a suitable source, isolation and identification of the microorganisms and cultivation of the identified bacteria and so on.

(3) METHOD (3-1) Preparation of Preincubated Cultures

From each of the preservation slants of the concerned microorganisms, a loop of the respective strain was taken out and spreaded onto GAM agar culture medium (by Nissui Seiyaku), and unaerobically cultivated for 16 hours at 35° C. Colonies grown on each GAM agar medium were scraped by a platinum loop and suspended into physiological saline solution so as to provide a predetermined turbidity of 2.0 (wavelength: 660 nm) thereby preincubated cultures for respective strains were prepared.

(3-2) Tests for Growth-promoting Effects

Into purified water, GAM bouillon culture medium (by Nissui Seiyaku) was dissolved in the indicated concentration, and the resultant solution was sterilized at 115° C. for 15 minutes thereby basic culture medium was prepared. A plurality of test culture medium for each of lactoferrin-compounds prepared in step (1) were prepared by adding each of the lactoferrin-compounds so as to make 0.05% concentration of respective lactoferrin-compounds in the resultant culture medium.

To test culture medium, each of preincubated cultures prepared in step (3-1) was inoculated by 1% thereby test bacterial cultures were prepared. After measuring turbidities of the resultant test bacterial cultures, they were unaerobically incubated for 16 hours at 35° C., then the turbidities after incubation were measured again.

A plurality of control bacterial cultures were prepared in the same manner as the test bacterial cultures, except that purified water was added instead of lactoferrin-compounds solution, and turbidities thereof were measured in the same manner as in test bacterial cultures.

Growth-promoting rate (hereinafter abbreviated as G-P rate) was calculated by following formula:

$$\text{G-P rate (\%)} = (T16 - T0)/(C16 - C0) \times 100 - 100$$

wherein T16 means turbidity after 16 hours incubation of test bacterial culture, T0 means turbidity before incubation of test bacterial culture, C16 means turbidity after 16 hours incubation of control bacterial culture and C0 means turbidity before incubation of control bacterial culture.

(4) THE TEST RESULTS

The results are shown in Table 1.

TABLE 1

GROWTH-PROMOTING EFFECT OF HUMAN Fe-LACTOFERRIN, BOVINE LACTOFERRIN, BOVINE APOLACTOFERRIN AND BOVINE Fe-LACTOFERRIN FOR BEFIDOBACTERIA

| strains | G-P rate (%) | | | |
|---|---|---|---|---|
| | hFe-1f | bovine 1f | bovine apo-1f | bovine Fe-1f |
| B. bifidum | 15 | 53 | 62 | 48 |
| B. infantis | 14 | 54 | 63 | 49 |
| B. breve | 18 | 55 | 63 | 48 |
| B. longum | 17 | 56 | 60 | 48 |
| B. pseudolongum | 1 | 55 | 58 | 47 |
| B. animalis | 2 | 52 | 59 | 47 |

It will be understood from Table 1 that all of bovine lactoferrin (bovine lf in abbreviation), bovine apolactoferrin (bovine apo-lf in abbreviation) and bovine Fe-lactoferrin (bovine Fe-lf in abbreviation) have remarkably stronger growth-promotive activities to all of 6 strains of Bifidobacteria than human Fe-lactoferrin (hFe-lf in abbreviation). It will be also understood that human Fe-lactoferrin did not show growth-promoting activity upon Bifidobacteria derived from animals such as B. pseudolongum and B. animalis.

Test 2

This test was conducted to determine effective concentration of bovine lactoferrin, bovine apolactoferrin and bovine Fe-lactoferrin for growth-promoting activity.

(1) PREPARATION OF MATERIALS (1-1) Preparation of Bovine Lactoferrin

In the same manner as in step (1-1) of Test 1, bovine lactoferrin was prepared.

(1-2) Preparation of bovine apolactoferrin

In the same manner as in step (1-2) of Test 1, bovine apolactoferrin was prepared.

(1-3) Preparation of bovine Fe-lactoferrin

In the same manner as in step (1-3) of Test 1, bovine Fe-lactoferrin was prepared.

(2) TESTED STRAINS

The same strains in Test 1 were used.

(3) METHOD

The method was the same as in step (3-2) of Test 1, except that bovine lactoferrin, bovine apolactoferrin and bovine Fe-lactoferrin were respectively used in various concentrations as shown in Table 2. The G-P rates were calculated in the same manner as in Test 1.

(4) Results

The results are shown in Table 2.

shown in the concentration over 250–500 ppm both inclusive.

It has been found that bovine apolactoferrin showed the highest activity, bovine lactoferrin next and then bovine Fe-lactoferrin.

Now some examples will be described hereunder for better understanding of the present application.

EXAMPLE 1

Prepared was 2 l of culture medium for mass production of Bifidobacteria containing 1.0% of yeast extract, 1.5% of meat extract, 1.0% of casitone, 0.1% of potassium dihydrogen phosphate, 0.1% of dipotassium hydrogen phosphate, 0.7% of sodium acetate, and 3% of lactose, and 0.04% of cystine (respectively in weights). The resultant culture medium was sterilized at 115° C. for 15 minutes.

To 100 ml of purified water, 1 g of previously prepared bovine lactoferrin was dissolved and removed microorganisms which might be contaminated in the resulted lactoferrin solution by the sterile membrane filter. To the previously prepared culture medium, 40 ml of the resultant lactoferrin solution was added (bovine lactoferrin concentration in the medium was 196 ppm), then 1% of the preincubated culture of B. longum prepared in the same manner as in step (3-1) of test 1 was innoculated to obtain a test sample which was anaerobically incubated at 37° C. for 16 hours. Viable cell counts in the test medium was measured after incubation. A control sample was prepared in the same manner as in the test sample, except that purified water was added therein instead of bovine lactoferrin solution. The viable count after incubation was measured in the same manner as in the test sample.

The results are shown in Table 3. As will be seen from Table 3, the viable cell count was increased by 50% in the test sample in which bovine lactoferrin was added.

TABLE 3

EFFECT OF BOVINE LACTOFERRIN UPON GROWTH OF B. longum

| sample | viable count (/ml) |
|---|---|
| control | $30 \times 10^8$ |
| test (added bovine lactoferrin) | $45 \times 10^8$ |

EXAMPLE 2

In the same manner as in Example 1, viable cell counts were measured for test and control samples,

TABLE 2

GROWTH-PROMOTING EFFECTS OF BOVINE LACTOFERRIN-COMPOUNDS FOR BIFIDOBACTERIA

| | G-P rate (%) | | | | | | | | | | | | | | | | | | | | |
|---|---|---|---|---|---|---|---|---|---|---|---|---|---|---|---|---|---|---|---|---|---|
| | bovine lactogerrin (ppm) | | | | | | | bovine apolactoferrin (ppm) | | | | | | | bovine Fe-lactoferrin (ppm) | | | | | | |
| strains | 10 | 30 | 50 | 100 | 250 | 500 | 1000 | 10 | 30 | 50 | 100 | 250 | 500 | 1000 | 10 | 30 | 50 | 100 | 250 | 500 | 1000 |
| B. bifidum | 2 | 12 | 26 | 49 | 54 | 54 | 49 | 5 | 19 | 31 | 55 | 58 | 62 | 55 | 2 | 10 | 22 | 34 | 48 | 48 | 41 |
| B. infantis | 4 | 13 | 29 | 51 | 53 | 55 | 50 | 7 | 20 | 30 | 53 | 59 | 63 | 53 | 3 | 9 | 23 | 35 | 44 | 49 | 44 |
| B. breve | 4 | 11 | 29 | 50 | 55 | 55 | 50 | 5 | 22 | 29 | 54 | 57 | 62 | 55 | 3 | 9 | 22 | 36 | 43 | 47 | 40 |
| B. longum | 5 | 15 | 27 | 55 | 56 | 57 | 51 | 4 | 26 | 30 | 55 | 58 | 64 | 52 | 2 | 11 | 24 | 32 | 41 | 49 | 4 |
| B. pseudolongum | 3 | 16 | 27 | 50 | 54 | 55 | 51 | 2 | 25 | 28 | 54 | 56 | 50 | 53 | 1 | 8 | 21 | 31 | 42 | 46 | 42 |
| B. animalis | 3 | 15 | 25 | 47 | 51 | 52 | 49 | 2 | 20 | 28 | 51 | 57 | 60 | 51 | 1 | 8 | 20 | 33 | 40 | 46 | 41 |

From Table 2, it will be understood that all of bovine lactoferrin, bovine apolactoferrin and bovine Fe-lactoferrin have growth-promoting activities upon all of 6 strains of Bifidobacteria in a concentration more than 30 ppm inclusive, that the activities are proportional to the concentration, and that the maximum G-P rates were except that the former included bovine apolactoferrin (the concentration of bovine apolactoferrin was 196 ppm) and the latter included purified water instead thereof. The results are shown in Table 4. As will be seen from Table 4, the viable count was increased by 66% in the test sample.

TABLE 4

EFFECT OF BOVINE APOLACTOFERRIN UPON GROWTH OF B. longum

| sample | viable count (/ml) |
|---|---|
| control | $30 \times 10^8$ |
| test (added bovine apolactoferrin) | $50 \times 10^8$ |

EXAMPLE 3

In the same manner as in Example 2, viable cell counts were measured for test and control samples, except that preincubated culture of B. pseudologum prepared in the same manner as in step (3-1) of Test 1 instead of B. longum (the concentration of bovine apolactoferrin was 196 ppm). The results are sown in Table 5. As will be seen from Table 5, the viable count was increased by 62% in the test sample.

TABLE 5

EFFECT OF BOVINE APOLACTOFERRIN UPON GROWTH OF B. pseudolongum

| sample | viable count (/ml) |
|---|---|
| control | $42 \times 10^8$ |
| test (added bovine apolactoferrin) | $68 \times 10^8$ |

EXAMPLE 4

A mixture of bovine lactoferrin and bovine apolactoferrin was prepared using those prepared in Test 1. The growth-promoting effect of the mixture was measured in the same manner as in Example 1, except that the mixture was used instead of bovine lactoferrin alone (concentration of bovine lactoferrin was 98 ppm and that of bovine apolactoferrin was 98 ppm in the medium). The results are shown in Table 6. As will be seen from Table 6, it will be understood that the viable count was increased by 63% in the test sample.

TABLE 6

EFFECT OF A MIXTURE OF BOVINE LACTOFERRIN AND BOVINE APOLACTOFERRIN UPON GROWTH OF B. longum

| sample | viable count (/ml) |
|---|---|
| control | $30 \times 10^8$ |
| test (added the mixture of bovine lf and bovine apo-lf) | $68 \times 10^8$ |

EXAMPLE 5

To 1 kg of aqueous solution of skim milk pasteurized at 80° C. for 10 minutes (solid content of skim milk in the resultant solution was 8.2%), 2% of commercially available yogurt starter (YB-15, by CHR.HANSEN'S LABORATORIUM) prepared in accordance with the instruction attached, 0.2 g of bovine lactoferrin prepared in Test 1, 1% of preincubated culture of B. longum obtained in Example 1 were added and aseptically dispenced by 100 ml into yogurt cups, then they were fermented at 40° C. for 5 hours thereby test samples of yogurt were prepared (concentration of bovine lactoferrin was 200 ppm). Control samples were also prepared in the same manner as in test samples, except that bovine lactoferrin was not added. The viable cell counts of Bifidobacterium and lactic acid bacteria under preservation at 5° C. were measured immediately after preparation of yogurt and at 7th, 10th and 14th days thereafter. The results are shown in Table 7. The viable counts of Bifidobacterium after preparation (0 day) were higher in the yogurt included bovine lactoferrin and its survivability under preservation was also better therein.

TABLE 7

VIABLE CELL COUNTS OF BIFIDOBACTERIUM IN YOGURT AND SURVIVABILITY THEREOF UNDER PRESERVATION (BOVINE LACTOFERRIN ADDED)

| sample | count of Bifidobacterium (/g) | | | | count of lactic acid bacteria (/g) | | | |
|---|---|---|---|---|---|---|---|---|
| | 0 day | 7th | 10th | 14th | 0 day | 7th | 10th | 14th |
| control | $30 \times 10^6$ | $55 \times 10^5$ | $20 \times 10^3$ | $>10^2$ | $20 \times 10^7$ | $17 \times 10^7$ | $13 \times 10^7$ | $12 \times 10^7$ |
| test (added b. lf) | $10 \times 10^7$ | $60 \times 10^6$ | $73 \times 10^5$ | $13 \times 10^5$ | $19 \times 10^7$ | $17 \times 10^7$ | $14 \times 10^7$ | $12 \times 10^7$ |

EXAMPLE 6

Yogurt samples for control and test were prepared in the same manner as in Example 5, except that 0.3 g of bovine apolactoferrin prepared in Test 1 was used instead of bovine lactoferrin (the concentration of bovine apolactoferrin in the yogurt was 300 ppm). The viable cell counts of Bifidobacteria and lactic acid bacteria were measured immediately after preparation of yogurt and at 7th, 10th and 14th days thereafter under preservation at 5° C. The results are shown in Table 8. The viable counts of Bifidobacterium after preparation (0 day) were higher in the yogurt included bovine apolactoferrin and its survivability under preservation was also better therein.

TABLE 8

VIABLE CELL COUNTS OF BIFIDOBACTERIUM IN YOGURT AND SURVIVABILITY THEREOF UNDER PRESERVATION (BOVINE APOLACTOFERRIN ADDED)

| sample | count of Bifidobacterium (/g) | | | | count of lactic acid bacteria (/g) | | | |
|---|---|---|---|---|---|---|---|---|
| | 0 day | 7th | 10th | 14th | 0 day | 7th | 10th | 14th |
| control | $31 \times 10^6$ | $50 \times 10^5$ | $25 \times 10^3$ | $>10^2$ | $21 \times 10^7$ | $18 \times 10^7$ | $14 \times 10^7$ | $13 \times 10^7$ |
| test | $12 \times 10^7$ | $99 \times 10^6$ | $65 \times 10^6$ | $11 \times 10^6$ | $20 \times 10^7$ | $18 \times 10^7$ | $15 \times 10^7$ | $13 \times 10^7$ |

EXAMPLE 7

Yogurt samples for control and test were prepared in the same manner as in Example 6, except that preincubated culture of B. pseudolongum used in Example 3 was used instead of B. longum (the concentration of bovine apolactoferrin in yogurt was 300 ppm). The viable cell counts of Bifidobacterium and lactic acid bacteria were measured immediately after preparation of yogurt and at 7th, 10th and 14th days thereafter under preservation at 5° C. The results are shown in Table 9. The viable counts of Bifidobacterium after preparation (0 day) were higher in the yogurt included bovine apolactoferrin and its survivability under preservation was also better therein.

TABLE 9

VIABLE CELL COUNTS OF BIFIDOBACTERIUM IN YOGURT AND SURVIVABILITY THEREOF UNDER PRESERVATION (BOVINE APOLACTOFERRIN ADDED)

| sample | count of Bifidobacterium (/g) | | | | count of lactic acid bacteria (/g) | | | |
|---|---|---|---|---|---|---|---|---|
| | 0 day | 7th | 10th | 14th | 0 day | 7th | 10th | 14th |
| control | $40 \times 10^6$ | $30 \times 10^6$ | $25 \times 10^6$ | $21 \times 10^6$ | $19 \times 10^7$ | $18 \times 10^7$ | $16 \times 10^7$ | $15 \times 10^7$ |
| test | $11 \times 10^7$ | $11 \times 10^7$ | $10 \times 10^7$ | $9 \times 10^7$ | $20 \times 10^7$ | $20 \times 10^7$ | $17 \times 10^7$ | $15 \times 10^7$ |

EXAMPLE 8

Yogurt samples for control and test were prepared in the same manner as in Example 5, except that a mixture of 0.1 g of bovine lactoferrin and 0.1 g of bovine apolactoferrin prepared in Test 1 was added instead of bovine lactoferrin in Example 5 (the concentration of bovine lactoferrin was 100 ppm and that of bovine apolactoferrin was 100 ppm). The viable cell counts of Bifidobacterium and lactic acid bacteria under preservation at 5° C. were measured immediately after preparation of yogurt and at 7th, 10th and 14th days thereafter. The results are shown in Table 10. The viable counts of Bifidobacterium after preparation (0 day) were higher in the yogurt included the mixture of bovine lactoferrin and bovine apolactoferrin and its survivability under preservation was also better therein.

TABLE 10

VIABLE CELL COUNTS OF BIFIDOBACTERIUM IN YOGURT AND SURVIVABILITY THEREOF UNDER PRESERVATION (A MIXTURE OF B. LACTOFERRIN AND B. APOLACTOFERRIN)

| sample | count of Bifidobacterium (/g) | | | | count of lactic acid bacteria (/g) | | | |
|---|---|---|---|---|---|---|---|---|
| | 0 day | 7th | 10th | 14th | 0 day | 7th | 10th | 14th |
| control | $30 \times 10^6$ | $52 \times 10^5$ | $23 \times 10^3$ | $>10^2$ | $19 \times 10^7$ | $20 \times 10^7$ | $16 \times 10^7$ | $15 \times 10^7$ |
| test | $13 \times 10^7$ | $80 \times 10^6$ | $86 \times 10^5$ | $42 \times 10^5$ | $20 \times 10^7$ | $17 \times 10^7$ | $15 \times 10^7$ | $15 \times 10^7$ |

EXAMPLE 9

To 800 g of skim milk powder, 200 g of powdery bovine lactoferrin prepared in the same manner in step (1-1) of Test 1 was added to thereby obtain 1000 g of an easily fluidal powdery composition of the present invention.

The resultant composition was fed to 5 healthy Holstein cows of 1-2 years ages, twice a day for 2 days together with ordinary feed in the morning and in the afternoon by 30 g at a time.

Viable bacterial counts per g of the feces before and after ingestion of bovine lactoferrin were compared. The results are shown in Table 11.

From Table 11, it will be understood that viable bacterial counts of harmful intestinal bacteria were reduced, and that those of useful Bifidobacteria were increased by the dosage of bovine lactoferrin.

TABLE 11

VIABLE BACTERIAL COUNTS PER g OF FECES (BOVINE LACTOFERRIN)

| cow No. | E. coli | | C. perfringens | | Bifidobacterium | |
|---|---|---|---|---|---|---|
| | before | after | before | after | before | after |
| 1 | $73 \times 6$ | $10 \times 6$ | $41 \times 6$ | $20 \times 5$ | $61 \times 6$ | $48 \times 7$ |
| 2 | $61 \times 7$ | $22 \times 6$ | $56 \times 6$ | $11 \times 6$ | $22 \times 6$ | $11 \times 7$ |
| 3 | $25 \times 7$ | $71 \times 6$ | $31 \times 6$ | $82 \times 5$ | $43 \times 6$ | $39 \times 7$ |

TABLE 11-continued

VIABLE BACTERIAL COUNTS PER g OF FECES (BOVINE LACTOFERRIN)

| cow No. | E. coli | | C. perfringens | | Bifidobacterium | |
|---|---|---|---|---|---|---|
| | before | after | before | after | before | after |
| 4 | $81 \times 6$ | $44 \times 6$ | $75 \times 5$ | $19 \times 5$ | $12 \times 7$ | $66 \times 7$ |
| 5 | $73 \times 7$ | $36 \times 7$ | $82 \times 5$ | $21 \times 5$ | $39 \times 6$ | $22 \times 7$ |

EXAMPLE 10

Added 150 g of powdery bovine apolactoferrin prepared in the same manner in step (1-2) of Test 1, to 850 g of skim milk powder to thereby obtain 1000 g of easily fluidal composition of the present invention.

To 5 healthy Holstein cows of 1-2 years ages, the resultant composition was fed twice a day for 2 days together with ordinary feed in the morning and in the afternoon by 30 g at a time.

Viable bacterial counts per g of the feces before and after ingestion of bovine apolactoferrin were compared. The results are shown in Table 12.

From Table 12, it will be understood that viable counts of harmful intestinal bacteria were reduced, and that those of useful Bifidobacteria were remarkably increased by the dosage of bovine apolactoferrin.

TABLE 12

VIABLE BACTERIAL COUNTS PER g OF FECES (BOVINE APOLACTOFERRIN)

| cow No. | E. coli | | C. perfringens | | Bifidobacterium | |
|---|---|---|---|---|---|---|
| | before | after | before | after | before | after |
| 1 | $43 \times 6$ | $49 \times 5$ | $33 \times 6$ | $20 \times 5$ | $52 \times 6$ | $82 \times 7$ |
| 2 | $56 \times 11$ | $22 \times 5$ | $26 \times 6$ | $55 \times 5$ | $37 \times 6$ | $61 \times 7$ |
| 3 | $29 \times 7$ | $33 \times 6$ | $52 \times 6$ | $81 \times 5$ | $16 \times 6$ | $75 \times 7$ |
| 4 | $81 \times 6$ | $96 \times 5$ | $46 \times 5$ | $12 \times 5$ | $56 \times 5$ | $39 \times 7$ |
| 5 | $76 \times 7$ | $15 \times 6$ | $90 \times 5$ | $15 \times 5$ | $13 \times 7$ | $21 \times 8$ |

EXAMPLE 11

Added 300 g of powdery bovine FE-lactoferrin prepared in the same manner in step (1-3) of Test 1, to 700 g of skim milk powder to thereby obtain 1000 g of easily fluidal composition of the present invention.

To 5 healthy Holstein cows of 1-2 years ages, the resultant composition was fed twice a day for 2 days together with ordinary feed in the morning and in a the afternoon by 30 g at a time.

Viable bacterial counts per g of the feces before and after ingestion of bovine Fe-lactoferrin were compared. The results are shown in Table 13.

From Table 13, it will be understood that viable bacterial counts of harmful intestinal bacteria were reduced, and that those of useful Bifidobacteria were remarkably increased by the dosage of bovine Fe-lactoferrin.

TABLE 13

VIABLE BACTERIAL COUNTS PER g OF FECES (BOVINE Fe-LACTOFERRIN)

| cow | E. coli | | C. perfringens | | Bifidobacterium | |
|---|---|---|---|---|---|---|
| No. | before | after | before | after | before | after |
| 1 | $72 \times 6$ | $41 \times 6$ | $43 \times 6$ | $24 \times 6$ | $32 \times 6$ | $2 \times 7$ |
| 2 | $61 \times 7$ | $39 \times 7$ | $21 \times 6$ | $10 \times 6$ | $88 \times 5$ | $56 \times 6$ |
| 3 | $27 \times 7$ | $11 \times 7$ | $35 \times 6$ | $26 \times 6$ | $46 \times 6$ | $17 \times 7$ |
| 4 | $54 \times 6$ | $34 \times 6$ | $77 \times 5$ | $19 \times 5$ | $67 \times 5$ | $35 \times 6$ |
| 5 | $63 \times 7$ | $37 \times 7$ | $81 \times 5$ | $33 \times 5$ | $79 \times 6$ | $43 \times 7$ |

EXAMPLE 12

Added 100 g of powdery bovine lactoferrin and 100 g of bovine apolactoferrin prepared in the same manner in steps (1-1) and (1-2) of Test 1, to 800 g of skim milk powder to thereby obtain 1000 g of easily fluidal composition of the present invention.

To 5 healthy Holstein cows of 1-2 years ages, the resultant composition was fed twice a day for two days together with ordinary feed in the morning and in the afternoon by 30 g at a time.

Viable bacterial counts per g of the feces before and after ingestion of the mixture of bovine lactoferrin and bovine apolactoferrin were compared. The results are shown in Table 14.

From Table 14, it will be understood that viable counts of harmful intestinal bacteria were reduced, and that those of useful Bifidobacteria were remarkably increased by the dosage of the mixture of bovine lactoferrin and bovine apolactoferrin.

TABLE 14

VIABLE BACTERIAL COUNTS PER g OF FECES (BOVINE LACTOFERRIN MIXTURE OF AND BOVINE APOLACTOFERRIN)

| cow | E. coli | | C. perfringens | | Bifidobacterium | |
|---|---|---|---|---|---|---|
| No. | before | after | before | after | before | after |
| 1 | $93 \times 6$ | $56 \times 5$ | $43 \times 6$ | $16 \times 5$ | $39 \times 6$ | $59 \times 7$ |
| 2 | $71 \times 7$ | $22 \times 6$ | $64 \times 6$ | $27 \times 5$ | $91 \times 5$ | $29 \times 7$ |
| 3 | $57 \times 7$ | $19 \times 6$ | $35 \times 6$ | $13 \times 5$ | $43 \times 6$ | $78 \times 7$ |
| 4 | $30 \times 6$ | $63 \times 5$ | $76 \times 5$ | $10 \times 5$ | $66 \times 5$ | $42 \times 7$ |
| 5 | $67 \times 7$ | $48 \times 6$ | $70 \times 5$ | $11 \times 5$ | $81 \times 6$ | $16 \times 8$ |

From the foregoing tests and examples, it will be understood that the bioactive agnets consisting of one or more bovine lactoferrin-compounds selected from the group consisting of bovine lactoferrin, bovine apolactoferrin and bovine Fe-lactoferrin and the compositions comprising the agents as the effective component can be used in various purposes in various aspects.

Although only a limited number of tests and examples have been described herein, it should be noted that the present invention should not be limited thereto, but various modifications and alterations can be made without departing from the concepts of the present invention.

It will be apparent to those skilled in the art that the present invention provides not only the bioactive agents but also the compositions, materials and products to which the bioactive agent are added as the effective component or ingredient to afford the growth-promoting activity to Bifidobacteria and to increase survivability of Bifidobacteria when they are included therein.

EFFECTS OF THE INVENTION

The effects of the present invention are as follows:
(1) The bioactive agents in accordance with the present invention may promote proliferation of Bifidobacteria.
(2) The bioactive agents in accordance with the present invention can be added to materials in which Bifidobacteria are to be inoculated or included, for example, culture medium for Bifidobacteria, foods or feeds to promote proliferation and/or to improve survivability thereof.
(3) The agents of the present invention can be given to humanbeings and other animals as it is or in combination with vehicles or carriers for preparation, foods and feeds to increase Bifidobacteria in the intestine.

What is claimed is:

1. A culture medium for cultivation of Bifidobacteria, comprising at least 30 ppm of lactoferrin compound selected from the group consisting of bovine lactoferrin,, bovine apolactoferrin, bovine Fe-lactoferrin, and a mixture thereof, and a culture medium for incubation of Bifidobacteria.

2. A composition of matter, comprising at least 200 ppm of lactoferrin compound selected from the group consisting of bovine lactoferrin, bovine apolactoferrin, bovine Fe-lactoferrin, and a mixture thereof, at least 2% of a starter of Bifidobacteria, and the rest of edible material.

3. A composition for fermented milk, comprising at least 2% of a starter of Bifidobacteria, at least 200 ppm of a lactoferrin compound selected from the group consisting of bovine lactoferrin, bovine apolactoferrin, bovine Fe-lactoferrin, and a mixture thereof, and the rest of an aqueous solution of milk.

4. A method of promoting the growth of Bifidobacteria in the intestine, comprising orally administering at least 9 g/day of a lactoferrin compound selected from the group consisting of bovine lactoferrin, bovine apolactoferrin, bovine Fe-lactoferrin, and a mixture thereof to animals.

5. The culture medium for cultivation of Bifidobacteria of claim 1, comprising at least 50 ppm of a lactoferrin compound.

6. The culture medium for cultivation of Bifidobacteria of claim 1, comprising at from 250-500 ppm of a lactoferrin compound.

7. The composition of matter of claim 2, comprising at least 300 ppm of lactoferrin compound.

8. The composition of fermented milk of claim 3, comprising at least 300 ppm of a lactoferrin compound.

9. The method of claim 4, wherein said animal is a cow.

10. The method of claim 4, wherein said animal is a human being.

11. The culture medium of claim 1, further comprising Bifidobacteria.

12. The method of claim 4 wherein treatment of Bifidobacteria comprises orally administering said bovine lactoferrin compound to humans or animals.

* * * * *